Figure 1:
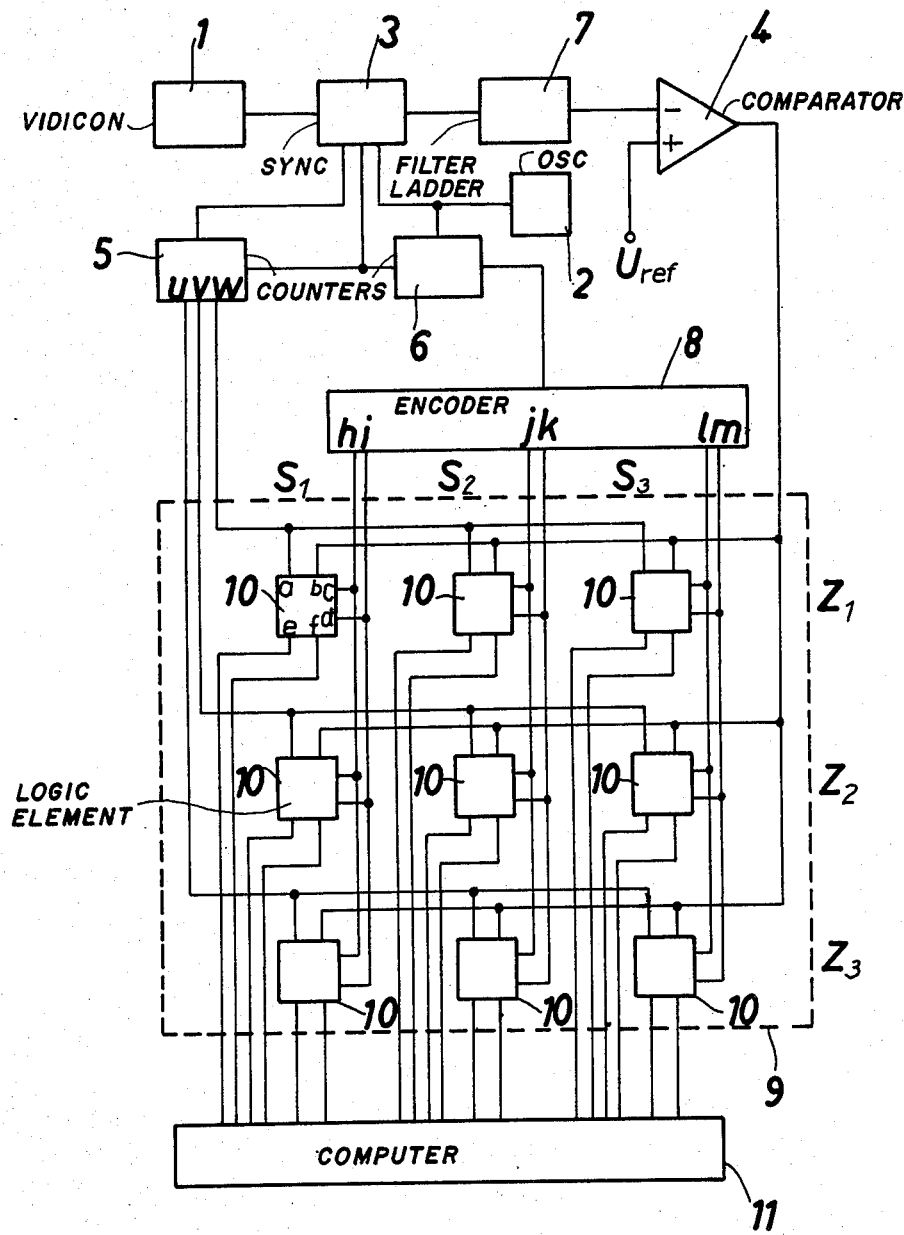

United States Patent [19]

Altmann et al.

[11] 4,238,767
[45] Dec. 9, 1980

[54] ARRANGEMENT FOR MEASURING THE MOBILITY OF IMAGE POINTS OF A VIDEO IMAGE

[75] Inventors: Jürgen Altmann; Heidrun Sanke; Günter Schöppe, all of Jena; Wolfgang Schütt, Rostock, all of German Democratic Rep.

[73] Assignee: Jenoptik Jena G.m.b.H., Jena, German Democratic Rep.

[21] Appl. No.: 17,959

[22] Filed: Mar. 6, 1979

[30] Foreign Application Priority Data

Mar. 10, 1978 [DD] German Democratic Rep. .................................... 0120412

[51] Int. Cl.³ .............................................. H04N 7/18
[52] U.S. Cl. ................................... 358/107; 358/93; 358/903; 364/515
[58] Field of Search ............... 358/107, 106, 101, 93, 358/903; 364/515; 235/92 MY, 92 PC

[56] References Cited

U.S. PATENT DOCUMENTS

| | | | |
|---|---|---|---|
| 3,978,324 | 8/1976 | Rayner | 358/107 |
| 4,079,416 | 3/1978 | Faani | 358/106 |
| 4,115,806 | 9/1978 | Morton | 358/107 |
| 4,159,522 | 6/1979 | Zanoni | 364/515 |

Primary Examiner—Howard W. Britton

[57] ABSTRACT

The invention is concerned with an arrangement for measuring the mobility of image points of a video image, particularly for the evaluation of the electrophoretic mobility of particles. The arrangement simultaneously evaluates an entire image contents of a plurality of image points without the necessity of subjectively preselecting individual image points.

The digitilized image signal of the video image is logical combined with the line and column scanning signals of the video image in a logic matrix and the obtained signals are fed into a computer via a time storage. The scanning signals are derived from a pulse generator and from the image synchronizing and line synchronizing signals. The logic combination of the signals also includes a direction selection member for programming the evaluation direction of the image points.

3 Claims, 2 Drawing Figures

ARRANGEMENT FOR MEASURING THE MOBILITY OF IMAGE POINTS OF A VIDEO IMAGE

The invention relates to an arrangement for measuring the mobility of image points of a video image, in which a vidicon and a pulse generator are coupled to a synchronizing circuit, the outputs of which are connected to two counters, and to a comparator for feeding the image signals of the video images thereinto via a filter ladder. The outputs of the counters and of the comparator are connected to a logic circuit which in turn is coupled to a computer. It is known from the Zeitschrift für physikalische Chemie, Vol. 356 to measure the mobility of a great number of particles simultaneously, however, an analyse of the speed distribution of the individual particles can only be approximated statistically.

The particles are required to move in a close formation under conditions which are difficult to realise so that very limited application conditions exist.

Furthermore, devices are known which perform mobility measurements by use of laser Doppler methods.

The electronic and optical expenditures involved therein are considerable, and the simultaneous measurement of the mobility of a plurality of particles lacks definition (Nzgiris E. E. (1972) Optics Commun 6).

Furthermore, there are image evaluation methods known in which the mobility of objects is measured in off-line operation (refer, for example, to Hall, Endlich, Wolf, Brain "Objective methods for registering landmarks and determining Cloud motions from satellite data", IEE Trans. Corp., July 1972). Said methods require photographic exposures at constant time intervals and an expensive intermediate storing of the single images, and, therefore, cannot be employed for real time measurements.

In a further known method for measuring the electrophoretic mobility of particles (WP G 1 N/200 932) a moving video image is real-time evaluated.

A subjectively selected particle located in an electrophoresis cell, moves a measuring distance established by two electronically realised thresholds.

The transit time of the respective particle is subject to a time measurement under microscopic observation and monitoring. It is of disadvantage that the single particle measurements require a considerable long time to find out of a great number of measurements a mean value to obtain a representative result for the sample material investigated.

Furthermore, the measuring arrangement has to be prepared for a selected image point by setting the measuring distance which is both time and work consuming.

Furthermore, a method for pattern recognition is known from the journal Radio, Fernsehen, Elektronik 25, 1976, copy 2, page 63 to 66, in which a television image is scanned, the image information digitalised, linewise stored in a buffer, fed into a computer or further processed in a real-time operation.

This method is disadvantageous since a great number of informations per image are offered which require high technical expenditures.

It is an object of the invention to reduce the expenditures for time and operation, and to increase the precision in image interpretation of liquid samples.

It is a further object of the invention to provide an arrangement for measuring the mobility of image points of a video image with considerably simple means and with the least possible operation requirements.

It is still a further object of the invention to evaluate simultaneously an entire image contents in two horizontal directions without a subjective pre-selection of individual image points with respect to a considerably great number of image points.

The invention relates to an arrangement for mobility measurements of image points of a video image, comprising a video camera and a pulse generator being connected to a synchronizing circuit, the outputs of which are connected to a first and a second counter and to a comparator via a filter ladder for the image signal of the video image, the outputs of the first and second counter and of the comparator are connected to a logic circuit, the output of which being connected to a computer, characterised in that the logic circuit consists of a matrix constituted of AND-elements to which the output of the comparator and, one output of the first and of the second counter are coupled, and in that each of two neighbouring AND-elements is followed by a gate element, the trigger input of which being connected to a respective output of a direction selecting element, the input of which is connected via an OR-member to the outputs of the two neighbouring gate elements and the two output signals of which are in logic opposition, and in that each gate element is followed by a time storage the output of which is connected to the computer.

It is of advantage when the input of the direction selecting element is connected to the clock pulse input of a D-type flip-flop which is set via its set-inputs and wherein a first output of said D-type flip-flop is connected to a first input of a first and second AND-element and each set input of the D-type flip-flop are connected to an OR-element via an AND-element and timing element, and via a further AND-element, respectively.

The output of said OR-element is connected to the clock pulse input of one of the two gate circuits following the two neighbouring AND-elements.

By virtue of the inventional arrangement the video-image is electronically scanned and the scanning signals are logically combined with the image signal of the video image with low technical and economical expenditures.

The output signals of the logic circuit are fed into a computer via a timing storage. The image points of a digitalised image signal during an entire image passage are involved into the logic operation.

This ensures a simultaneous evaluation of all image point motions.

The directional movements of the image points for evaluation are programmed via the direction selecting elements.

Figure 2:
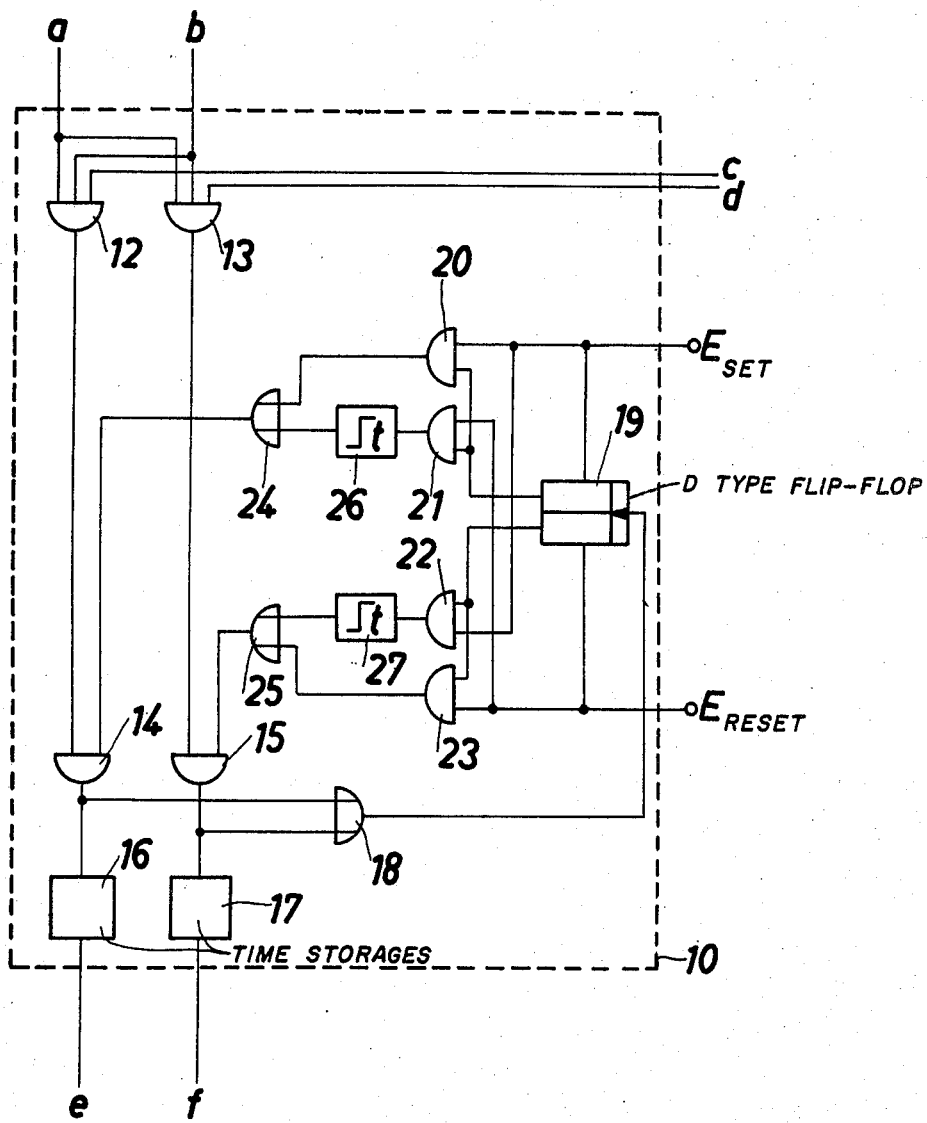

In order that the invention may be more readily understood reference is made to the accompanying drawings which illustrate diagrammatically and by way of example one embodiment thereof and in which FIG. 1 is a schematic view of a circuit arrangement for measuring the mobility of image points of a video image taken from liquid samples, FIG. 2 is a logic circuit of the arrangement of FIG. 1.

In FIG. 1 a vidicon 1 produces a video image of, for example, an electrophoretic sample. The resulting signal is fed into a synchronizing member 3 which is connected via one output to a quartz oscillator 2. A further output of the synchronizing member 3 is connected to a comparator 4 via a filter ladder 7.

A reference voltage $U_{ref}$ is applied to the other input of the comparator 4.

A second output of the synchronizing member 3 is connected both, to a counter 5 and to a counter 6, a third output is only connected to the counter 5, and the output establishing the connection to the quartz oscillator 2 is only coupling the counter 6. The counter 6 is followed by an encoder 8 the six outputs h; i; j; k; l; m of which and the three outputs u, v, w of the counter 5 and the output of the comparator 4 are connected to the lines and/or columns of a logic matrix 9.

The logic matrix 9 consists of nine identically constructed logic circuit elements 10 arranged in three lines $Z_1$, $Z_2$, $Z_3$ and three columns $S_1$, $S_2$, $S_3$.

The circuitry of the element 10 is shown in more detail in FIG. 2.

Each input a of the three logic elements 10 in the line $Z_1$ is connected to the output w of the counter 5, whereas the inputs a of the logic elements 10 in the second line $Z_2$ are connected to the output v and the inputs a in the line $Z_3$ to the output u of the counter 5.

The output b of each logic element 10 is coupled to the output of the comparator 4.

Furthermore the c inputs of the logic elements 10 are connected in the column $S_1$ to the output h in the column $S_2$ to the output j, and in the column $S_3$ to the output 1 of the encoder element 8.

In analogy thereto the inputs d of the logic elements 10 are coupled to the encoder element 8, hence the column $S_1$ is connected to the output i, the column $S_2$ to the output k and the column $S_3$ to the output m.

The outputs e and f of each logic element are fed into a computer 11.

As can be seen from FIG. 2, both, inputs a and b of the logic circuit 10 are connected to the inputs of the AND-elements 12 and 13. The third input of the AND-element 12 is the input c, whereas the input d is connected to the third input of the AND-element 13.

The output of the AND-element 12 is connected to a first input of an AND-element 14, the output of which is connected via a time storage 16 to the output e.

Similarly, the AND-member 13 is followed by an AND-member 15, the output of which is connected via a time storage 17 to the output f.

Furthermore, the two outputs of the AND-members 14, 15 are coupled to two inputs of an OR-member 18, the output of which is connected to the clock-pulse input of a D-type flip-flop 19.

One output of the D-type flip-flop 19 is connected to the respective one inputs of the AND-members 20, 21 in analogy thereto the other output of the D-type flip-flop is connected to the AND-members 22, 23.

The second input of the AND-members 20, 22 and the set-input of the D-type flip-flop 19 are connected to the set input $E_{set}$.

A second set input $E_{reset}$ is connected to the reset input of the D-type flip-flop 19 and to the second inputs of the AND-members 21, 23.

The output of the AND-member 20 is connected to one input of an OR-member 24, the output of the AND-member 23 to one input of the OR-member 25.

A connection is established via a time member 26 between the output of the AND-member 21 and the second input of an OR-member 24, the output of which is connected to an input of an AND-member 14.

A further time member 27 connects the AND-member 22 to the second input of the OR-member 25 the output of which is coupled to the second input of the AND-member 15.

The set inputs $E_{set}$ of all logic members 10 are connected with each other, just as the set inputs $E_{reset}$ (not shown in the drawing for more simplicity).

The quartz oscillator 2 controls the counter 6 and the synchronizing member 3 which produces the vertical and the horizontal synchronization pulses.

The synchronizing pulses control the vidicon 1 in known manner which produces a video image of a mobile object, for example, of a sample under electrophoretic test.

The image signal of the video image is fed into the filter ladder 7 which, predominantly forwards the frequency spectrum of the mobile object (band-pass filter).

The filtered image signal is fed into the comparator 4, the reference threshold is set by means of the reference voltage $U_{ref}$ to values which correspond to definite grey stages of the mobile object.

When the signal level exceeds the reference voltage $U_{ref}$ at the inverting input of the comparator 4 the latter delivers a signal which is applied to all logic circuits 10 of the logic matrix 9.

The counter 6 and the subsequent encoding member 8 derives six pulses at the outputs h, i, j, k, l, m, in each line of the video image in dependence from the clock pulse of the quartz oscillator 2 and the line synchron pulse of the synchronizing member 3.

Then uneven pulses substantially divide the video image in sequence into four equal parts.

The distance between the even numbered and the uneven numbered pulses can be varied by means known per se and not shown in the drawing in steps which are about one hundred and twenty fifth (1/125) of the line length.

The counter 5 which is reset by the vertical synchronization pulse counts the lines of the so-called half image which are produced through line scanning of each second line of the video image.

When the lines 20 to 100 are concerned the output w delivers a signal, when the line 120 to 200 are concerned the output v delivers a signal and when the lines 220 and 300 of the video image are concerned the output u delivers a signal.

The output pulses from the counters 5, 6 and from the comparator 4 are combined through AND-members in the logic circuits 10 of the matrix 9.

The output signals of said AND-members 12, 13 are fed via the gate circuits constituted of the AND-members 14, 15 into the time storages 16, 17 in which the points of time of the logic combination of the signals are stored at via the inputs a, b, c, and a, b, d, respectively, of the logic circuits.

The outputs of the time storages 16, 17 are fed into the computer 11 for difference formation via the outputs e, f of each logic circuit 10 so to obtain the time variations or, in connection with a unit of length, the mobility of the image points.

The D-type flip-flop 19, the AND-members 20, 21, 22, 23 the time elements 26, 27 and the OR-members 18, 24, 25 constitute in cooperation with the AND-members 14, 15 a direction selection unit for time, respectively, speed measurement of the image points so that the computation detection of the image points has not only to be carried out in a definite horizontal direction of movement.

The output pulses of the counter 6 can be represented on the monitor as gates by means not shown in the drawing and known per se.

In order to explain the mode of operation of the direction selecting unit it is assumed that the time storage 16 of FIG. 2 is provided for time measurements at a first gate where a pulse is applied at the input c of the logic circuit 10 and the time storage 17 functions as time measuring at a second gate where the pulse is applied to the input d of the logic circuit 10.

When the direction selecting unit has, for example, actuated the AND-member 14, the motion of the image points can be traced from the first to the second gate.

In the event of the AND-combination of the three signals at the inputs a, b, c that is, an image point passes the first gate in the line range of the video image to be scanned, this point of time is stored in the time storage 16. At the same time the D-type flip-flop 19 is switched over through the OR-member 18 so that the AND-member 14 is OFF and the AND-member 15 is ON.

The setting ON of the AND-member 15 can be time delayed by means of the time member 27 the time constant of which is adjustable.

Provided that suitable logic combinations are performed the AND-members 20, 21, 22, 23 and the OR-members 24, 25 actuate the second gate, considered in motion direction, at a delayed time.

When the image points move from the first gate to the second gate the image point which actuates the first gate will be the next to arrive at the second gate.

Image points which are not detected at the first gate are substantially eliminated by the dead time of the second gate in cooperation with the time member 27.

All objects the transition time of which exceed the given time limit actuate the second gate. At the same time the output pulse from the AND-member 15 registered in the time storage 17 resets the D-type flip-flop to its starting position so that the AND-member 14 is prepared for the next measuring operation.

The direction selection is programmed via a corresponding signal at the control input $E_{set}$ and the control input $E_{reset}$, respectively, and is simultaneously executed for all logic circuits 10.

We claim:

1. Arrangement for measuring the mobility of particles, comprising
    a vidicon,
    a synchronizing circuit having two inputs and three outputs, the vidicon being connected to the first input of said synchronizing circuit,
    a first counter having two inputs and a first output, a second output, and a third output,
    a second counter having two inputs and one output, the first output of the synchronizing circuit being connected to the first input of said first counter, the second output of said synchronizing circuit being connected to the second input of said first counter and to the first input of said second counter,
    a pulse generator, being connected to the second input of said synchronizing circuit, and to the second input of said second counter,
    an encoder having one input and six outputs, the output of said second counter being connected to the input of said encoder,
    a filter ladder connected to the third output of said synchronizing circuit,
    a comparator being provided with a reference voltage, said comparator being connected to the output of said filter ladder,
    nine logic circuits having each four inputs and two outputs,
    a logic matrix constituted of said nine logic circuits, said nine logic circuits being arranged in three lines and three columns,
        the three logic circuits arranged in the first line of said logic matrix being connected via their first inputs to said first output of said first counter, the three logic circuits arranged in the second line of said logic matrix being connected via their first inputs to said second output of said first counter, the three logic circuits arranged in the third line of said logic matrix being connected to said third output of said first counter,
        the second outputs of said nine logic circuits being connected to the output of said comparator, the three logic circuits arranged in the first column of said logic matrix being connected via the third inputs to the first output of said encoder, and via the fourth inputs to the second output of said encoder,
        the three logic circuits arranged in the second column of said logic matrix being connected via the third inputs to the third output of said encoder, and via the fourth inputs to the fourth output of said encoder, the three logic circuits arranged in the third column of said logic matrix being connected via the third inputs to the fifth output of said encoder, and via the fourth inputs to the sixth output of said encoder,
    a computer, the two outputs of said nine logic circuits being connected to said computer.

2. Arrangement as claimed in claim 1, wherein each of said nine logic circuits comprises
    a first AND-element having three inputs and one output, said three inputs being connected to first, second and third inputs of said logic circuits,
    a second AND-element having three inputs and one output, said three inputs being connected to first, second and fourth inputs of said logic circuits
    a third AND-element having two inputs and one output, the output of said first AND-element being connected to the first input of said third AND-element,
    a fourth AND-element having two inputs and one output, the output of said second AND-element being connected to the first input of said fourth AND-element,
    a first storage,
    a second storage, the output of said third AND-element being connected to the first output of said logic circuit via said first storage, the output of said fourth AND-element being connected to the second output of said logic circuit via said second storage,
    a first OR-element having two inputs and one output,
    a direction selection circuit having an input, a first control input and a second control input, a first output, and a second output,
        the output of said third AND-element being connected to the first input of said first OR-element,
        the output of said fourth AND-element being connected to the second input of said first OR-element, said input of said direction selection circuit being connected to the output of said first OR-element,
said first output of said direction selection circuit being connected to the second input of said third AND-element,
said second output of said direction selection circuit being connected to the second input of said fourth AND-element.

3. Arrangement as claimed in claim 2, wherein said direction selection circuit of each logic circuit comprises
a flip-flop having a trigger input,
a set-input and a reset-input and a first and a second output,
a fifth AND-element, having a first and a second input, and an output,
a sixth AND-element having a first and a second input,
a seventh AND-element having a first input and a second input, and an output,
an eighth AND-element, having a first input and a second input, and an output,
said trigger input of said flip-flop being connected to the output of said first OR-element,
said first control input being connected to said set input of said flip-flop and to said first input of said fifth AND-element and to said first input of said seventh AND-element,
said second control input being connected to said reset input being in turn connected to said first input of said sixth AND-element and to said first input of said eighth AND-element,
said first output of said flip-flop being connected to the second inputs of said fifth and said sixth AND-element,
said second output of said flip-flop being connected to the second inputs of said seventh and said eighth AND-element,
a first timing-element,
a second timing-element,
a second OR-element having a first and a second input, and an output,
a third OR-element having a first and a second input and an output,
said output of said fifth AND-element being on-line connected to said first input of said second OR-element, said output of said sixth AND-element being connected to said second input of said second OR-element via said first timing element,
said output of said seventh AND-element being on-line connected to said first input of said third OR-element, said output of said eighth AND-element being connected to said second input of said third OR-element via said second timing element,
the output of said second OR-element being connected to the second input of said third AND-element, the output of said third OR-element being connected to the second input of said fourth AND-element.

* * * * *